(12) United States Patent
Cope (10) Patent No.: US 7,717,707 B2
(45) Date of Patent: May 18, 2010

(54) ORTHODONTIC TRANSPALATAL INTRUSION ARCH ASSEMBLY AND METHOD OF USE

(75) Inventor: Jason B. Cope, Dallas, TX (US)

(73) Assignee: Under Dog Media, L.P., Dallas, TX (US)

( * ) Notice: Subject to any disclaimer, the term of this patent is extended or adjusted under 35 U.S.C. 154(b) by 0 days.

(21) Appl. No.: 11/691,960

(22) Filed: Mar. 27, 2007

(65) Prior Publication Data
US 2007/0231766 A1    Oct. 4, 2007

Related U.S. Application Data

(60) Provisional application No. 60/788,224, filed on Mar. 31, 2006.

(51) Int. Cl.
*A61C 7/00* (2006.01)
(52) U.S. Cl. .................. 433/18; 433/7; 433/24
(58) Field of Classification Search .......... 433/6, 433/7, 18, 20, 21, 24
See application file for complete search history.

(56) References Cited

U.S. PATENT DOCUMENTS

| | | | |
|---|---|---|---|
| 1,908,853 A | 10/1930 | Linde | |
| 3,162,948 A * | 12/1964 | Gerber | 433/7 |
| 3,792,529 A | 2/1974 | Goshgarian | |
| 4,202,100 A | 5/1980 | Forster | |
| 4,392,826 A | 7/1983 | Goshgarian | |
| 4,408,989 A | 10/1983 | Cleary | |
| 4,592,725 A | 6/1986 | Goshgarian | |
| 5,007,828 A * | 4/1991 | Rosenberg | 433/18 |
| 5,816,800 A | 10/1998 | Brehm et al. | |
| 5,967,772 A * | 10/1999 | Gray | 433/7 |
| 6,908,306 B2 * | 6/2005 | Bowman et al. | 433/18 |
| 2003/0104335 A1 * | 6/2003 | Chung | 433/18 |
| 2005/0221249 A1 * | 10/2005 | Keles | 433/18 |

* cited by examiner

*Primary Examiner*—Cris L Rodriguez
*Assistant Examiner*—Michael R Ballinger
(74) *Attorney, Agent, or Firm*—Sanford E. Warren, Jr.; Akin Gump Strauss Hauer & Feld

(57) ABSTRACT

An improved transpalatal arch wire assembly comprising a transpalatal arch wire, wherein the transpalatal arch wire comprises a first vertically sloping component, a second vertically sloping component, and a intermediate adjustment section disposed between the first and second vertically sloping components; and a first auxiliary wire coupled to the transpalatal arch wire, wherein the first auxiliary wire is substantially rigid and defines a first attachment arm approximate to an end of the first auxiliary wire, wherein the first attachment arm is suitable for receiving an orthodontic force module.

20 Claims, 5 Drawing Sheets

ORTHODONTIC TRANSPALATAL INTRUSION ARCH ASSEMBLY AND METHOD OF USE

CROSS REFERENCE TO RELATED APPLICATIONS

This application claims the benefit of U.S. Provisional Application Ser. No. 60/788,224, filed Mar. 31, 2006, entitled: ORTHODONTIC TRANSPALATAL INTRUSION ARCH ASSEMBLY AND METHOD OF USE by inventor Jason B. Cope.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCES TO A "SEQUENCE LISTING"

Not applicable.

BACKGROUND OF THE INVENTION

The present invention relates to the field of orthodontic appliances, and more particularly to an improved, removable and adjustable transpalatal arch wire capable of accurately transmitting correctional intrusion forces to a pair of brackets mounted on opposing molars.

In the straightening of teeth by an orthodontist, a commonly encountered malocclusion is a skeletal open bite, which is caused by misaligned upper and lower jaws. A skeletal open bite is characterized in a person whose upper and lower front and side teeth do not close together, but only the back two teeth (the first and second molars) on the top and bottom jaws come together and touch, making it difficult for the person to chew food or to close their mouth.

Orthodontists have heretofore used vertical elastics from the upper front teeth to the lower front teeth in an attempt to close the front and side teeth together vertically. Unfortunately, the front and side teeth usually relapse to the pretreatment condition after the elastics are removed. Moreover, long-term heavy elastic wear in these types of cases has been associated with root resorption (root shortening), thereby causing damage to the teeth. Another approach employed jointly by orthodontists and oral surgeons is for the orthodontist to straighten the teeth first and subsequently the oral surgeon performs jaw surgery to properly align the jaws. This, however, is an extremely expensive treatment, has the inherent risk of postoperative paresthesia (numbness), and more importantly has the added risk of possible death when the patient is put to sleep for surgery.

Palatal arch wires currently utilized can be used to connect the upper back first molars together and create movement about the teeth, but do not allow simultaneous intrusive forces to be applied to said molars. For example, because the molars are connected across the arch, bending the arch wire to place an intrusive force on one of the connected molars simultaneously places an extrusive force on the other molar due to Newton's third law—for every for action there is an equal and opposite reaction. Further, the amount of intrusion possible with such arch wires is no more than 0.5-1.0 mm at most. For treatment of a skeletal open bite, back molar intrusion requires an average of 3-7 mm, depending on the severity of the open bite.

Improvements to palatal arch wires have included the addition of a U-shaped locking bar to prevent dislodgement from the brackets, thereby allowing it to also be attached to the second molars. Such locking bars also defined an arm or hook for receiving an elastic for applying forces to other teeth. Because all the upper teeth lie in a horizontal line, connecting the elastic from the palatal arch wire to other upper teeth only allows horizontal forces to be applied to the palatal arch wire connected teeth, which will not aid in correcting a skeletal open bite. The same elastic force, if connected from the palatal arch wire hook to the lower teeth, would actually create an extrusive force on the palatal arch wire connected teeth, which would make the open bite worse. Another problem with the locking bar is that it must be bent away from the tooth to allow bracket insertion, then bent back toward the tooth for locking to prevent dislodgement. This same action must occur every time the palatal arch wire is removed for adjustment, predisposing the locking bar to fatigue failure and breakage because of continued adjustment.

Because of the proximity of the locking bar/hook to the bracket connected to the palatal arch wire, a force exerted via an elastic could only be applied close to the molar to which it is attached. Since a skeletal open bite is characterized by the back first and second molars touching, the best location for an intrusive force is between these teeth anteroposteriorly. Such a solution is not yet in the art.

What has been introduced is a simpler insertion of the palatal arch wire into the bracket by employing a round horizontal wire. In order to provide for mediolateral control of tooth movement, or torque, a vertically oriented bar was attached to the round insertion wire on both sides of the interconnecting arch wire. However, this is not always ideal. For example, in patients with canted occlusal planes, where the teeth are lower on one side of the mouth than the other, intrusion is desired on one side only. In this case, the palatal arch wire should only have a vertically oriented bar on the side of the mouth where intrusion is desired. The opposite side should have no vertically oriented bar so that the wire can simply rotate inside the bracket tube without applying torque.

Recently, orthodontic temporary anchorage devices have been used to improve tooth movement. An orthodontic temporary anchorage device is a device that is temporarily fixed to bone structure for the specific purpose of enhancing and providing sufficient orthodontic anchorage either by supporting the teeth of the reactive unit or by obviating the need for the reactive unit altogether, and which is subsequently removed after use. In orthodontics, a temporary anchorage device refers to all variations of implants, screws, pins and plates placed specifically for the purpose of providing orthodontic anchorage and can be removed upon completion of biomechanical therapy. Orthodontic temporary anchorage devices are useful when applied in the correction of dental discrepancies, which include anteroposterior tooth movements, molar uprighting, and intrusion/extrusion of single and multiple teeth. Orthodontic temporary anchorage devices can also be useful in the correction of oral skeletal discrepancies, as in the case of a skeletal open bite. There exists a need however for a mechanism of connecting the teeth, or orthodontic appliances thereon, to the orthodontic temporary anchorage devices.

BRIEF SUMMARY OF THE INVENTION

The present invention is directed to an improved transpalatal arch wire as utilized in, but not limited only thereto, orthodontic applications, particularly with the application of orthodontic temporary anchorage devices. The present invention overcomes problems and difficulties previously encountered when a connecting mechanism from orthodontic temporary anchorage devices to orthodontic appliances is lacking, specifically when a connecting mechanism is lacking when using a palatal arch wire.

According to one aspect of the present invention, an improved orthodontic transpalatal arch wire assembly comprises a standard transpalatal arch wire wherein at least one auxiliary wire assembly is attached to provide for orthodontic force module attachment. In particular, the transpalatal arch wire assembly of the present invention can be used in connection with orthodontic temporary anchorage devices for correction of dental and skeletal discrepancies.

The present invention comprises a transpalatal arch wire assembly, wherein the assembly can be attached to at least the upper first molars, upper second molars and/or the upper premolars, and further comprises at least one auxiliary wire attached to a main arch wire to provide a capability for moving the point of force application away from a specific tooth to which the transpalatal arch wire is attached into a variety of locations. Moreover, the auxiliary wire assembly provides a means of applying an intrusive force to the teeth when used in combination with orthodontic temporary anchorage devices.

The auxiliary wire assembly according to one embodiment approximates an L-shaped form having a hook disposed thereon, preferably on at least one distal end thereof. The L-shaped auxiliary wire comprises at least three components comprising a base arm, an extension arm, and an attachment arm, wherein the extension arm is interposed with the base arm and the attachment arm. A substantial portion of the base arm is attached along its longitudinal axis to the longitudinal axis of a vertical component of the transpalatal arch wire. The extension arm further extends horizontally away from the base arm toward the upper second molar. The terminal end of the extension arm is connected to the attachment arm, which is usually in the form of a wire doubled over on itself to form a hook. The attachment arm is designed to function as the focal point for force application to receive an orthodontic force module from a temporary anchorage device so as to create an intrusive force on the upper first and second molars.

In another embodiment of the present invention, a vertical component of the transpalatal arch wire has an integrally attached housing with which the base arm of the auxiliary wire assembly is connected therewith, thereby allowing the removable insertion of auxiliary wire assemblies comprising a plurality of different lengths, diameters, or geometries.

DETAILED DESCRIPTION OF THE INVENTION

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the present invention.

The claims and specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

Figure 1A:
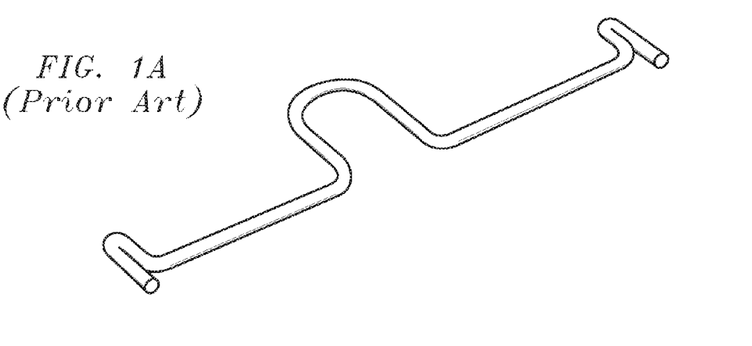
FIG. 1A is a perspective view of a transpalatal arch wire according to one embodiment of prior art.
Figure 1B:
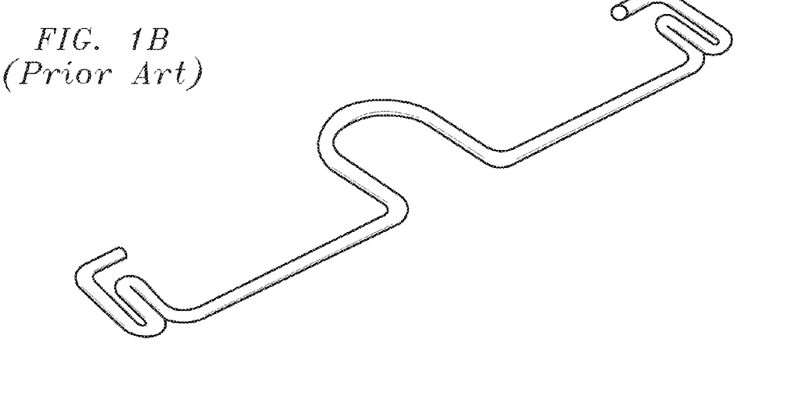
FIG. 1B is a perspective view of a transpalatal arch bar according to another embodiment of prior art.
Figure 1C:
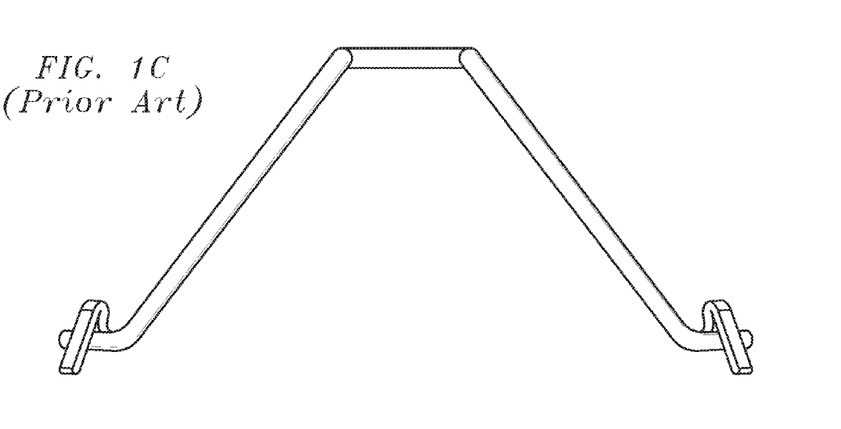
FIG. 1C an elevational view of a transpalatal arch wire according to yet another embodiment of prior art.

Referring to prior art FIGS. 1A, 1B, and 1C, various embodiments of transpalatal arch wires and bars are shown for reference. Such transpalatal arch wires and bars shown in FIGS. 1A-1C are generally known in the art. As with such known devices, transpalatal arch wires and/or bars generally include a wire that is chosen for its ability to exert a resilient spring-like force when formed with, but not limited to, a U-shaped loop or other similar design in the center of the wire/bar and having ends specifically bent or formed in a manner to provide an attachment point for attaching the wire/bar to sheaths mounted on molars. Although such devices have been used for some time, the manner in which the art has employed them cannot meet the needs of the technique of the present invention.

Figure 2:
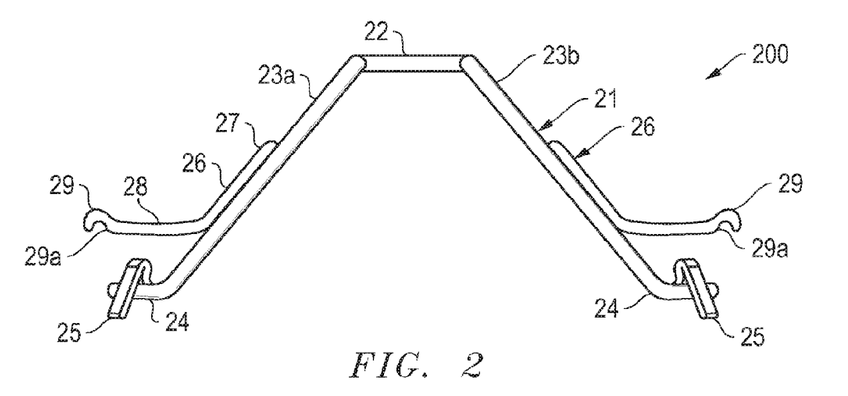
FIG. 2 is an elevational view of one embodiment of an improved orthodontic transpalatal arch wire assembly having auxiliary wire assemblies according to an embodiment of the present invention.
Figure 3A:
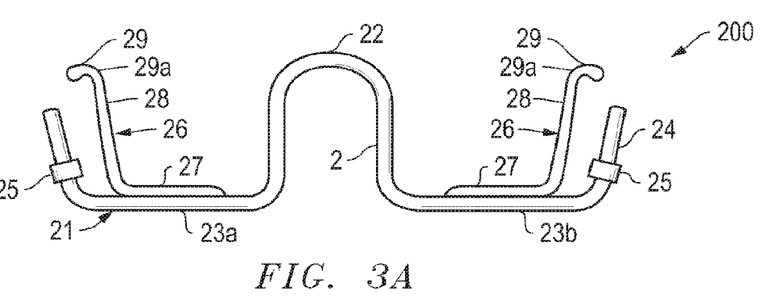
FIG. 3A is a bottom view of the improved orthodontic transpalatal arch wire assembly having auxiliary wire assemblies, when the improved orthodontic transpalatal arch wire assembly is rotated forward along a longitudinal central axis approximately 90 degrees, as compared to the elevational view of the embodiment shown in FIG. 2 according to the present invention.

Referring now to FIG. 2 and FIG. 3A, wherein FIG. 2 depicts an elevational view of one embodiment of an improved orthodontic transpalatal arch wire having auxiliary wire assemblies according to one embodiment of the present invention and wherein FIG. 3A depicts the same embodiment of the improved transpalatal arch wire assembly 200 but in a rotated view. Specifically, the embodiment shown and described in relation to FIG. 2 is now depicted in FIG. 3A such that the same embodiment has now been rotated in view approximately 90 degrees forward along a central longitudinal axis for further detailed explanation. The following detail is described with reference to both FIG. 2 and FIG. 3A.

The embodiment shown in FIGS. 2 and 3A of the present invention depicts an improved transpalatal wire assembly 200 comprising a transpalatal arch wire 21 and at least one auxiliary wire 26. It will be understood by one skilled in the art that more than one auxiliary wire 26 can be utilized to achieve various results.

Figure 4:
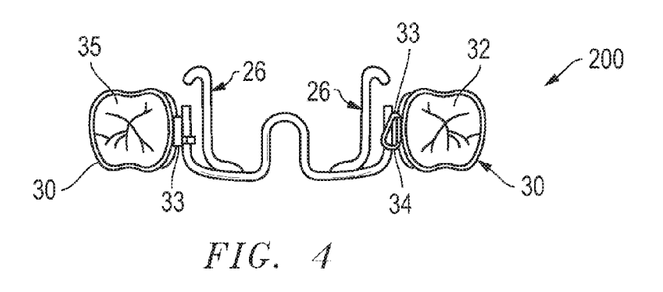
FIG. 4 is a bottom view of the improved orthodontic transpalatal arch wire of FIG. 3A when in a secured position with opposing molars according to an embodiment of the present invention.

The transpalatal arch wire 21 depicted in FIGS. 2 and 3A comprises at least two generally vertically sloping components 23a, 23b interconnected to each other by way of a shaped intermediate adjustment section 22. In the preferred embodiment, the shape of the intermediate adjustment section 22 is "U-shaped" but one skilled in the art will recognize that the embodiment is not limited only to a U-shape. The terminal ends of the two generally vertically sloping components 23a, 23b are each connected to a round wire insertion component 24 each having a constituent element bar 25 integrally attached thereto. The constituent element bar 25 serves to prevent over-insertion of the insertion component 24 into a bracket 33 (such as bracket 33 depicted in FIG. 4) on a molar 32 (such as molar 32 depicted in FIG. 4), to provide a mechanism for locking the insertion component 24 into the bracket 33 when ligated by a metal or elastic ligature 34 (as shown in FIG. 4) or similar ligation device and to further control the torque applied to the bracket 33 (such as shown in FIG. 4).

The auxiliary wire 26 embodiment depicted in FIGS. 2 and 3A forms an approximate L-shape but is not limited specifically thereto such an L-shape. The angle created by the auxiliary wire 26 can range from 0 degrees to 180 degrees. The auxiliary wire 26 comprises three components. Specifically, the auxiliary wire 26 comprises a base arm 27, an extension arm 28, and at least one attachment arm 29 disposed thereon at least a first end 29a of the extension arm 28, wherein the extension arm 28 is interposed with the base arm 27 and the attachment arm 29. It will be understood by one skilled in the art that all components of the enhanced transpalatal arch wire assembly 200 can be manufactured from materials such as, but not limited to, stainless steel, titanium, titanium alloy, or NiTi alloy, but preferably stainless steel.

Figure 6A:
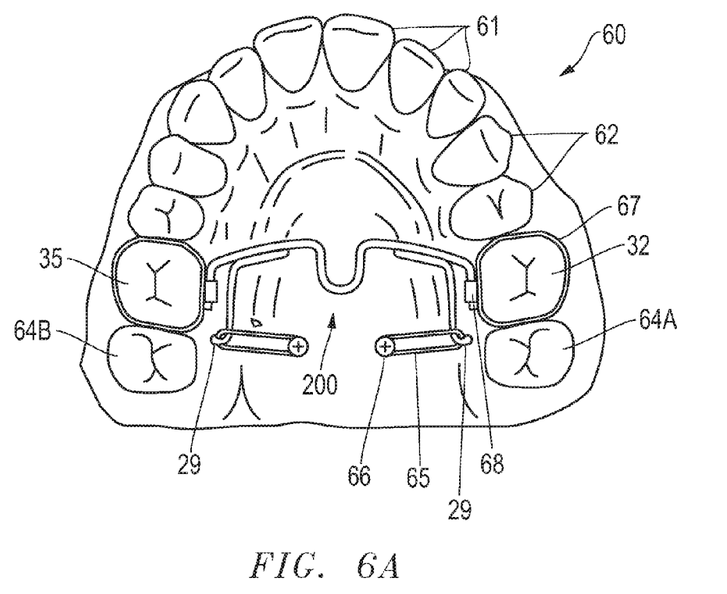
FIG. 6A is a bottom view of the improved orthodontic transpalatal arch wire shown in FIG. 3A when disposed in a pretreatment condition of a skeletal open bite according to an embodiment of the present invention.

A substantial portion of the length of the base arm 27 is mounted along the base arm's 27 longitudinal axis to the longitudinal axis of the two generally vertically sloping components 23a, 23b of the transpalatal arch wire 21. The attachment arm 29 is geometrically disposed on at least the first end 29a of the extension arm 28 and is designed to act as the point of force application to receive an orthodontic force module 65 (as shown in FIG. 6A) from a temporary anchorage device 66 (also shown in FIG. 6A) so as to create an intrusive force on the upper first molars 32, 35 (as shown in FIG. 6A) and second molars 64A, 64B (as shown in FIG. 6A). One skilled in the art will understand that the length and shape of the extension arm 28 can be varied to move the attachment arm 29 closer to or further away from the first molar 32, 35 or even fabricated so that the extension arm 28 and attachment arm 29 extends anteriorly toward the premolars 62 rather than posteriorly (as shown in FIG. 6A). This allows the point of force application on the attachment arm 29 to be moved into a variety of locations.

A person of ordinary skill in the art will understand that the auxiliary wire 26 described in reference to FIG. 2 and FIG. 3A can be designed and configured in a plurality of configurations for the purpose moving the point of force application via its attachment arm 29 to various positions in the mouth relative to connected first molars 63A, B (as shown in FIG. 6A). A person of ordinary skill in the art will also understand that the attachment arm 29 of the auxiliary wire assembly 26 can be formed in a variety of configurations for attachment of various orthodontic force modules 65 (as shown in FIG. 6A).

Figure 3B:
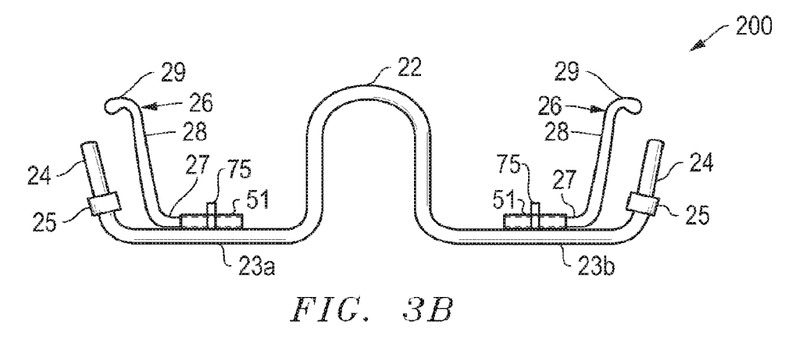
FIG. 3B is a bottom view of the improved orthodontic transpalatal arch wire of FIG. 3A, but wherein the orthodontic transpalatal arch wire shown comprises a base arm housing according to an embodiment of the present invention.
Figure 3C:
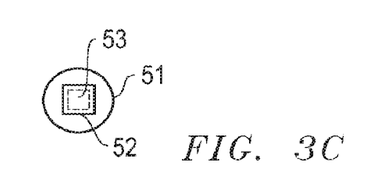
FIG. 3C is an enlarged end view of the base arm housing of the improved orthodontic transpalatal arch wire shown in FIG. 3B according to an embodiment of the present invention.

Now referring to FIG. 3B, an alternate method for providing attachment of auxiliary wire 26 is shown. However, one skilled in the art will understand that such alternate attachment method is also contemplated for use with other devices and embodiments of the present invention (for example, the embodiment shown in FIG. 2). The two generally vertically sloping components 23a, 23b of the improved transpalatal arch wire assembly 200 has an integrally attached base arm tube 51 in which the base arm 27 of the auxiliary wire 26 is inserted, thereby allowing the insertion of other auxiliary wires of different lengths, diameters, or geometries. Although not specifically depicted in FIG. 3B, it will be understood by one skilled in the art that the base arm tube 51 can also be configured with a small threaded hole to accept a removable set screw 75 that is oriented perpendicular to the longitudinal axes of the base arm tube 51 for removably securing the base arm 53 in place. A person of ordinary skill in the art will understand that, as depicted in FIG. 3B, the base arm tube 51 and the base arm 27 can have a plurality of different geometries. For example, as shown in FIG. 3C, a base arm tube 51 can have a square inner dimension 52 and a square base arm 53 cross-sectional dimension to provide a lock-and-key fit such that the inserted base arm 53 could not freely rotate in the base arm tube 51.

With reference now to FIG. 4, an example of the improved transpalatal arch wire assembly 200 in operational use as depicted in FIGS. 2 and 3A is shown and depicted. In FIG. 4, the improved transpalatal arch wire assembly 200 is reversibly attached via an elastic ligature 34 to a left molar 32 and a right molar 35 via brackets 33 attached to bands 30 cemented on said molars. Such reversible attachment allows easy removal of the improved transpalatal arch wire assembly 200 for adjustment. It will be understood by one skilled in the art that the improved transpalatal arch wire assembly 200 as shown in FIGS. 2 and 3A can also be similarly attached without departing from the scope and spirit of the present invention.

Figure 5A:
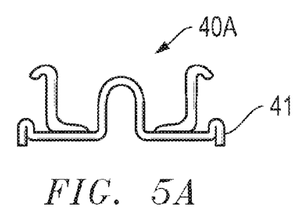
FIG. 5A is a bottom view of yet another embodiment of an improved orthodontic transpalatal arch wire having auxiliary wire assemblies according to the present invention.

Now referring to FIG. 5A, another embodiment of an orthodontic transpalatal arch wire assembly 40A is shown. In this embodiment, the insertion component 41 is a wire doubled over on itself to provide another method of insertion into a bracket 33 (as shown in FIG. 4) on a molar tooth.

Figure 5B:
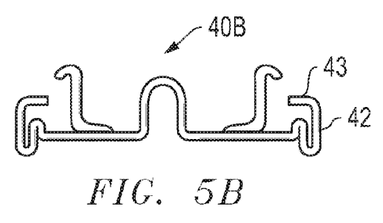
FIG. 5B is bottom view of yet another embodiment of an improved orthodontic transpalatal arch wire according to the present invention.

Now referring to FIG. 5B, yet another embodiment of an orthodontic transpalatal arch wire assembly 40B is shown. In the present embodiment, the insertion component 42 is a wire doubled over on itself with a locking bar 43 mechanism to provide another means of insertion into a bracket 33 (as shown in FIG. 4) on a molar tooth. The locking bar 43 provides a source of retention of the transpalatal arch wire assembly 40B, such that it prevents undesirable dislodgement. In addition, the locking bar 43 may act as an attachment point for elastics in various situations.

With reference now to FIG. 6A, an example of the improved transpalatal arch wire assembly 200 as depicted in FIGS. 2, 3A and 4 is shown and depicted in a post installation view. The improved transpalatal arch wire assembly 200 is shown reversibly attached to the upper left first molar 32 and upper right first molar 35 via brackets 68 attached to bands 67 cemented on the molars 32, 35. In this scenario, the upper anterior teeth 61 and premolar teeth 62 of the upper jaw 60 do not touch, but only the upper molars 32, 35 and 64A, 64B touch. The improved transpalatal arch wire assembly 200 is attached from its attachment arm 29 to an immobile orthodontic temporary anchorage device 66 via an orthodontic force module 65. The immobile temporary anchorage device 66 transmits an intrusive force via the orthodontic force module 65 to the brackets 68 connected to the bands 67 cemented on the molars 32, 35 through their attachment to the improved transpalatal arch wire assembly 200.

Figure 6B:
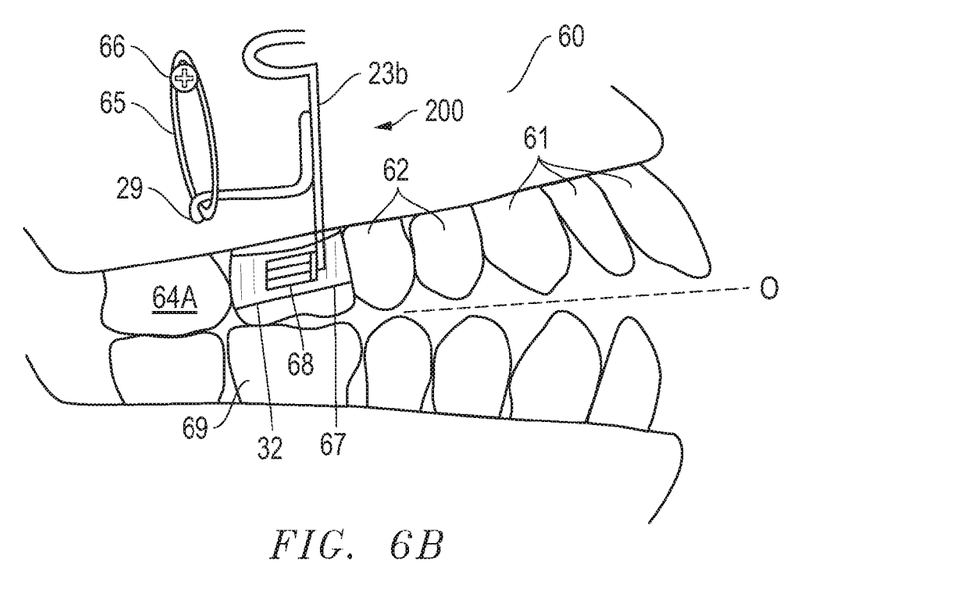
FIG. 6B is a side view of the left-half side of the improved orthodontic transpalatal arch wire depicted along a lateral midline aspect and in a pretreatment condition when disposed in a skeletal open bite according to an embodiment of the present invention.
Figure 6C:
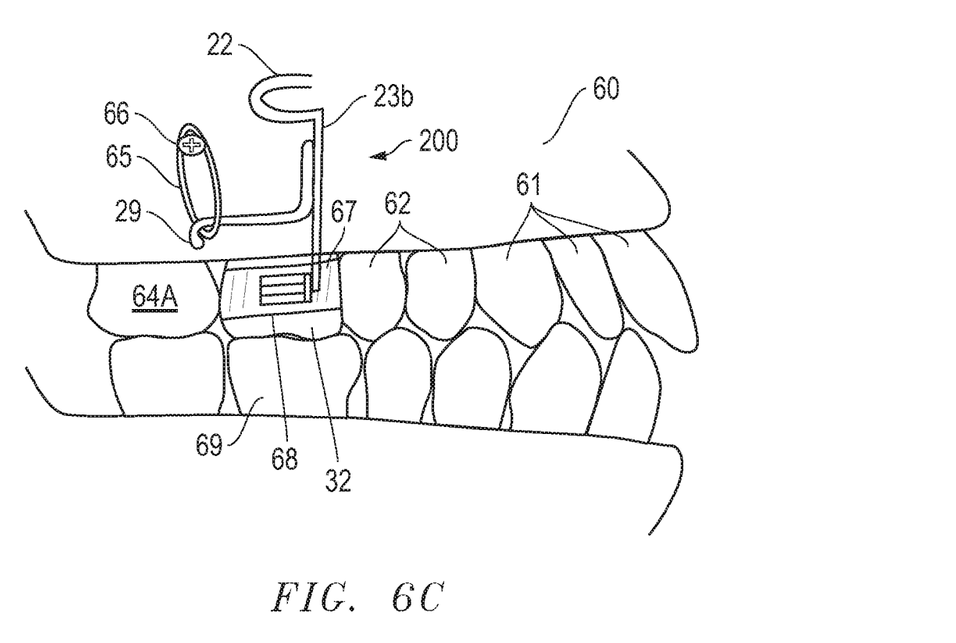
FIG. 6C is a side view of the left-half side of the improved orthodontic transpalatal arch wire shown in FIG. 6B along the lateral midline aspect but now depicted in a post-treatment condition when disposed in skeletal open bite correction according to an embodiment of the present invention.

An example of the improved transpalatal arch wire assembly 200 as depicted in FIGS. 2, 3A, 4 and 6A is further shown and depicted in FIGS. 6B and 6C from a lateral midline aspect, wherein only the left half of a patient's mouth is shown. In FIGS. 6B and 6C, the improved transpalatal arch wire assembly 200 is reversibly attached to the left upper molar 32 and right upper molar 35 (right upper molar 35 not shown in FIGS. 6B and 6C) via brackets 68 attached to bands 67 cemented on the left upper molar 32 and right upper molar 35. In this embodiment, the upper anterior teeth 61 and premolar teeth 62 of the upper jaw 60 do not touch, but only left upper molars 32, 64A and the right upper molars 35, 64B (35 and 64B are not shown in FIGS. 6B and 6C) contact lower molars 69.

In FIGS. 6B and 6C, the improved transpalatal arch wire assembly 200 is attached from its attachment arm 29 to the immobile orthodontic temporary anchorage device 66 via the orthodontic force module 65. The immobile orthodontic temporary anchorage device 66 transmits an intrusive force via the orthodontic force module 65 to upper molars 32 and 35 (35 not shown) through their attachment to the improved transpalatal arch wire assembly 200 to close an anterior open bite along line O as depicted in FIG. 6B. As depicted in FIG. 6C, the resultant open bite closure due to intrusion of the upper left molars 32 and 64A is evident.

Figure 7A:
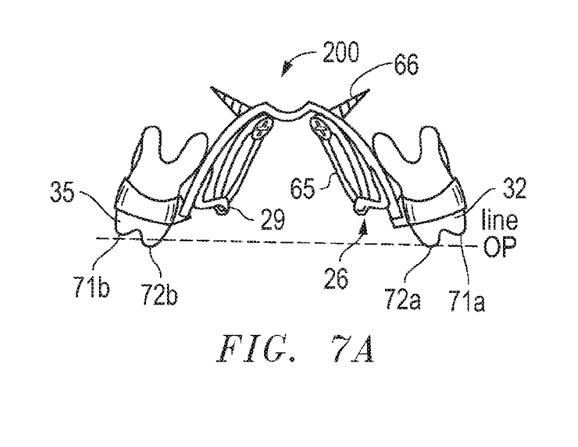
FIG. 7A is a front view of the improved orthodontic transpalatal arch wire of FIGS. 6A-6C depicted in a pretreatment condition of a skeletal open bite with reference to the occlusal plane according to an embodiment of the present invention.
Figure 7B:
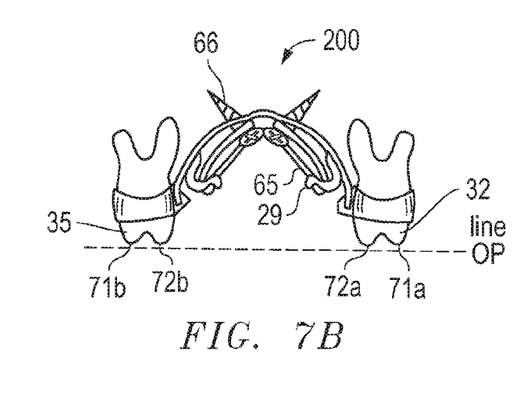
FIG. 7B is a front view of the improved orthodontic transpalatal arch wire of FIGS. 6A-6C but now depicted in a post-treatment condition of a skeletal open bite correction with reference to the occlusal plane according to an embodiment of the present invention.

Now referring to FIGS. 7A and 7B, an example of the improved transpalatal arch wire assembly 200 as depicted in FIG. 6A is shown and depicted as viewed from a frontal aspect. Open bite patients usually present with the lingual cusps 72a of the upper left first molar 32, and the lingual cusps 72b of the upper right first molar 35 hanging down below the occlusal plane line OP, and the buccal cusps 71a, 71b line up on the occlusal plane line OP. The lingual cusps 72a, 72b prematurely contact the lower molars 69 (not shown in FIGS. 7A and 7B, but is depicted above in FIGS. 6B and 6C) and exacerbate the open bite. When the improved transpalatal arch wire assembly 200 of the present invention is attached to the upper left first molar 32 and the upper right first molar 35 and is adjusted such that the point of force application applied to the attachment arm 29 is between the upper left first molar 32 and the upper right first molar 35 and left upper molars 64A and right upper molars 64B (as depicted in FIGS. 6B and 6C), the orthodontic force module 65 from the attachment arm 29 to the temporary anchorage device 66 applies and intrusive force which seats the lingual cusps 72a, 72b by moving them upward toward the occlusal plane, line OP. This results in closing the anterior open bite along line O (as shown in FIG. 6B) and allowing the upper anterior teeth 61 (as depicted in FIGS. 6B and 6C) to touch their lower counterparts in the front.

Figure 8A:
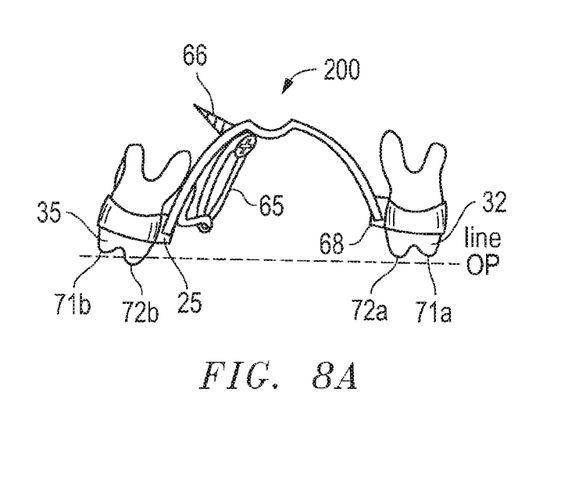
FIG. 8A is a front view of the improved orthodontic transpalatal arch wire of FIGS. 6A-6C depicted in a pretreatment condition of an occlusal cant according to an embodiment of the present invention.
Figure 8B:
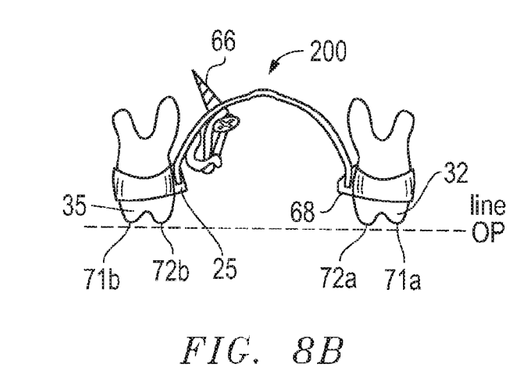
FIG. 8B is a front view of the improved orthodontic transpalatal arch wire of FIGS. 6A-6C but now depicted in a post-treatment condition of an occlusal cant correction according to an embodiment of the present invention.

Now referring to FIGS. 8A and 8B, an example of the improved transpalatal arch wire assembly 200 as depicted in FIGS. 2, 3A, 4 and 6A is shown and depicted as viewed from a frontal aspect. Another commonly encountered problem in orthodontics is the occlusal cant, which is characterized by the lingual cusps 72b of teeth on one side hanging down lower than the occlusal plane line OP than the lingual cusps 72a on the contralateral side. In this case, it is desirous to only intrude the lingual cusps 72b of the teeth on the upper right first molar 35. A person of ordinary skill in the art will understand that, because the insertion components of the prior art either have a doubled over wire which creates a rectangular geometry, or a constituent element bar rigidly attached to the insertion component, an intrusion force applied only to the right side of the orthodontic transpalatal arch assembly for intrusion of the right side lingual cusps will also transmit a force to the lingual cusps 72a of the upper left first molar 32, which will induce undesirable tooth movement of the upper left first molar 32.

Such a situation as described above can be avoided by using the embodiment described herein detailing the improved transpalatal arch wire assembly 200 with the constituent element bar 25 only on the right side and not on the left, such that the round wire insertion component 24 (not shown in FIGS. 8A and 8B) on the left side can freely rotate in its bracket tube 68, as an intrusive force is applied on the right side to the improved transpalatal arch wire assembly 200.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. It is therefore, contemplated that the claims will cover any such modifications or embodiments that fall within the true scope of the invention.

What is claimed is:

1. An improved transpalatal arch wire assembly comprising:
    a transpalatal arch wire, wherein the transpalatal arch wire comprises a first vertically sloping component, a second vertically sloping component, and a intermediate adjustment section disposed between the first and second vertically sloping components; and,
    a first auxiliary wire coupled to the transpalatal arch wire, wherein the first auxiliary wire is substantially rigid and comprises:
        a first base arm disposed at a first end of the first auxiliary wire;
        a first extension arm coupled to the first base arm to form an approximate L-shape; and
        a first attachment arm disposed at a second end of the first auxiliary wire and coupled to the first extension arm to form an approximate L-shape for receiving a first orthodontic force module, wherein the first orthodontic force module is independent of the first auxiliary wire;
    wherein the first base arm extends in a direction different from the first attachment arm; and, wherein a substantial portion of the length of the first base arm is mounted, along a longitudinal axis of the first base arm, to a longitudinal axis of one of the first and second vertically sloping components of the transpalatal archwire.

2. The improved transpalatal arch wire assembly of claim 1, further comprising a first round wire insertion component at a first end of the transpalatal arch wire and a second round wire insertion component at a second end of the transpalatal arch wire.

3. The improved transpalatal arch wire assembly of claim 2, further comprising a first constituent element bar coupled with the first round wire insertion component and a second constituent element bar coupled with the second round wire insertion component.

4. The improved transpalatal arch wire assembly of claim 1, wherein the first extension arm is interposed between the first base arm and the first attachment arm.

5. The improved transpalatal arch wire assembly of claim 4, further comprising a second auxiliary wire coupled to the transpalatal arch wire, wherein the second auxiliary wire comprises a second base arm disposed at a first end of the second auxiliary wire, a second extension arm coupled to the second base arm to form an approximate L-shape, and a second attachment arm disposed at a second end of the second auxiliary wire and coupled to the second extension arm to form an approximate L-shape for receiving a second orthodontic force module, wherein the second base arm extends in a direction different from the second attachment arm, and wherein the second orthodontic force module is independent of the second auxiliary wire.

6. The improved transpalatal arch wire assembly of claim 4, wherein a first angle is defined by the first base arm and the first extension arm.

7. The improved transpalatal arch wire assembly of claim 4, wherein the first base arm is fixedly attached to the transpalatal arch wire.

8. The improved transpalatal arch wire assembly of claim 7, wherein a portion of the first base arm is immediately adjacent and parallel to a portion of the transpalatal arch wire.

9. The improved transpalatal arch wire assembly of claim 4, further comprising a first base tube fixably attached to the transpalatal arch wire, wherein the first base arm of the first auxiliary wire is sized to be inserted into the first base tube.

10. The improved transpalatal arch wire assembly of claim 9, further comprising a first threaded screw disposed within the first base tube for securing the first base arm within the first base tube and keeping the first base arm from rotating within the first base tube.

11. The improved transpalatal arch wire assembly of claim 9, wherein the first base arm and the interior of the first base tube have securely fitting cross-sections, such that the first base arm is prevented from rotating within the first base tube.

12. A method of utilizing an improved transpalatal arch wire assembly, the method comprising the steps of:
    providing a transpalatal arch wire, wherein the transpalatal archwire comprises a first vertically sloping component, a second vertically sloping component, and an intermediate adjustment section disposed between the first and second vertically sloping components;
    providing a first auxiliary wire, wherein the first auxiliary wire comprises a first base arm disposed at a first end of the first auxiliary wire, a first extension arm coupled to the first base arm to form an approximate L-shape, and a first attachment arm disposed at a second end of the first auxiliary wire and coupled to the first extension arm to form an approximate L-shape for receiving a first orthodontic force module, wherein the first base arm extends in a direction different from the first attachment arm;
    attaching the first auxiliary wire to the transpalatal arch wire of the improved transpalatal arch wire assembly;
    inserting the transpalatal arch wire to first bracket secured to a first tooth and a second bracket secured to a second tooth; and
    attaching the first attachment arm to the first orthodontic force module, wherein the first orthodontic force module is independent of the first auxiliary wire, wherein a substantial portion of the length of the first base arm is mounted, along a longitudinal axis of the first base arm, to a longitudinal axis of one of the first and second vertically sloping components of the archwire.

13. The method of claim 12, further comprising moving the first auxiliary wire in a direction to apply an intrusion force to the first tooth and the second tooth by transmitting the intrusive force via the first orthodontic force module to the first and second brackets.

14. The method of claim 12, further comprising the step of:
    providing a second auxiliary wire, wherein the second auxiliary wire comprises a second base arm disposed at a first end of the second auxiliary wire, a second extension arm coupled to the second base arm to form an approximate L-shape, and a second attachment arm disposed at a second end of the second auxiliary wire and coupled to the second extension arm to form an approximate L-shape, wherein the second base arm extends in a direction different from the second attachment arm;

attaching the second auxiliary wire to the transpalatal arch wire of the improved transpalatal arch wire assembly, and attaching a second orthodontic force module between the second attachment arm and an immobile orthodontic temporary anchorage device, wherein the second orthodontic force module is independent of the second auxiliary wire.

15. The method of claim 14, further comprising the step of transmitting a second intrusive force via the second orthodontic force module to the first and second brackets.

16. The method of claim 15 directed toward correcting an anterior open bite, wherein the adjusting of the first and second auxiliary wires causes first and second intrusive forces to seat lingual cusps of the first tooth and the second tooth.

17. The method of claim 15 directed toward correcting occlusal cants, wherein the first bracket secured to a first tooth permits the transpalatal arch wire to rotate in the first bracket thereby causing first and second intrusive forces to be applied substantially to the second bracket.

18. The system of an improved transpalatal arch wire assembly in combination with an immobile orthodontic temporary anchorage device comprising:

a transpalatal arch wire, wherein the transpalatal arch wire defines a first vertically sloping component, a second vertically component, and a intermediate adjustment section disposed between the first and second vertically sloping components;

a first auxiliary wire coupled to the transpalatal arch wire, wherein the first auxiliary wire comprises a first base arm disposed at a first end of the first auxiliary wire, a first extension arm coupled to the first base arm to form an approximate L-shape, and a first attachment arm disposed at a second end of the first auxiliary wire and coupled to the first extension arm to form an approximate L-shape, wherein the first base arm extends in a direction different from the first attachment arm;

a first orthodontic bracket secured to a first tooth, wherein the first orthodontic bracket is reversibly attached to the transpalatal arch wire;

a first immobile orthodontic temporary anchorage device having a first orthodontic force module coupling the first immobile orthodontic temporary anchorage device, wherein the first orthodontic force module is independent of the first auxiliary wire; and, a first base arm tube in which the first base arm of the first auxiliary wire is inserted and, wherein a substantial portion of the length of the first base arm is mounted, along a longitudinal axis of the first base arm, to a longitudinal axis of one of the first and second vertically sloping components of the transpalatal archwire.

19. The system of claim 18, further comprising a second orthodontic bracket secured to a second tooth, wherein the second orthodontic bracket is reversibly attached to the transpalatal arch wire.

20. The system of claim 19, further comprising:

a second auxiliary wire coupled to the transpalatal arch wire, wherein the second auxiliary wire comprises a second base arm disposed at a first end of the second auxiliary wire, a second extension arm coupled to the second base arm to form an approximate L-shape, and a second attachment arm disposed at a second end of the second auxiliary wire and coupled to the second extension arm to form an approximate L-shape, wherein the second base arm extends in a direction different from the second attachment arm; and, a second immobile orthodontic temporary anchorage device having a second orthodontic force module coupling the second immobile orthodontic temporary anchorage device and the second attachment arm of the auxiliary wire, wherein the second orthodontic force module is independent of the second auxiliary wire.

* * * * *